United States Patent [19]

Workman, Jr. et al.

[11] 4,311,482

[45] Jan. 19, 1982

[54] METHOD AND APPARATUS FOR COLLECTING BLOOD SAMPLES

[75] Inventors: Erwin F. Workman, Jr., Vernon Hills; Deborah M. Clark, Gurnee, both of Ill.

[73] Assignee: Abbott Laboratories, North Chicago, Ill.

[21] Appl. No.: 82,840

[22] Filed: Oct. 9, 1979

[51] Int. Cl.$^3$ .................... G01N 33/16; C09K 3/00
[52] U.S. Cl. .................... 23/230 B; 23/902; 23/918; 252/408; 424/1; 424/2; 424/3; 424/12; 435/13
[58] Field of Search ............. 252/408; 23/230 B, 902, 23/918, 920; 422/58; 424/1, 2, 3, 12; 435/13

[56] References Cited

U.S. PATENT DOCUMENTS

| | | | |
|---|---|---|---|
| 4,090,977 | 5/1978 | Dubin | 252/408 |
| 4,195,072 | 3/1980 | Workman, Jr. | 252/408 |
| 4,213,876 | 7/1980 | Crews et al. | 252/408 |
| 4,219,440 | 8/1980 | Runck et al. | 252/408 |

OTHER PUBLICATIONS

Seeman, P., Biochemical Pharmacology, vol. 15, pp. 1753-1766, (1966).
Aledort, L. M. et al., Proc. Soc. Exp. Biol. Med., vol. 128, pp. 658-659, (1968).
Barn, Gvr., Human Blood Coagulation, Haemostasis and Thrombin, Biggs, R. Ed., Blackwell Scientific Pub. Landen, p. 184, (1976).
Nachmias, V. T., et al., Blood, vol. 53, No. 1, pp. 63-72, (Jan. 1979).
Ludlam, C. A., et al., Thrombosis Research, vol. 6, pp. 543-548, (1975).
Dawes, J., et al., Thrombosis Research, vol. 12, No. 5, pp. 851-861, (1978).
Handin, R. I. et al., J. Lab. Clin. Med., vol. 91, No. 2, pp. 340-349, (Feb. 1978).
Chesterman, C. N., et al., British J. Haematology, vol. 40, pp. 489-500, (1978).
Kaplan, K. A., et al., British J. Haematology, vol. 39, pp. 129-146, (1978).
O'Brien, J. R., J. Clin. Path., vol. 17, pp. 275-281, (1964).
O'Brien, J. R., J. Clin. Path., vol. 15, pp. 446-452, (1962).
Aledort, L. M., The Circulating Platelet, Johnson, S., Academic Press, N.Y., p. 268, (1975).
Abbott Laboratories, PF4 R1A, No. 93-5631/-R1-4-Rev., (Jan. 1979).
White, G. C., et al., J. Lab. Clin. Med., vol. 91, No. 1, pp. 76-82, (Jan. 1978).

*Primary Examiner*—Teddy S. Gron
*Attorney, Agent, or Firm*—John J. McDonnell

[57] ABSTRACT

This invention encompasses methods and apparatus for collecting blood samples. It has been discovered that p-aminobenzoyldiethylaminoethanol (procaine) is unexpectedly potent in stabilizing blood samples against platelet release reactions. Methods and apparatus of this invention are particularly useful for collecting blood samples for subsequent platelet factor 4 determination.

2 Claims, No Drawings

METHOD AND APPARATUS FOR COLLECTING BLOOD SAMPLES

BACKGROUND OF THE INVENTION

1. Field of the Invention

This invention relates to apparatus and methods for collecting blood which is to be used in screening tests for activation of the coagulation system. Platelet Factor 4 (PF4) is a small molecular weight protein that is secreted from the α-granules of platelets when cells undergo the release reaction. This phenomenon occurs when the platelets become activated subsequent to contact with subendothelial tissue and a variety of other physiological agents including thrombin, adenosine diphosphate and epinephrine. PF4 in a blood sample is measured using classical radioimmunoassay techniques. Unfortunately classical blood collection techniques result in activatin of the release mechanism in the collected blood sample. Great care must be exercised to insure that the release reaction measured is a result of activating the release reaction in vivo and not in vitro.

2. Prior Art

The prior art discloses a wide variety of techniques and approaches for stabilizing collected blood samples against platelet release reactions.

Careful handling of blood samples is required to inhibit the platelet release reaction. Generally the blood is collected by venipuncture techniques using standard EDTA (ethylenediaminetetraacetic acid) containing vacuum blood collection containers. The blood is mixed with the EDTA in the container by gentle inversion and the container is placed in an ice bath. After thirty minutes the sample is centrifuged at $2500 \times g$ and $2°-4°$ C. for twenty minutes. Centrifugation must take place within two hours after collection. The plasma is separated and analyzed directly or it can be stored at $2°-4°$ C. for 24 hours or at $-20°$ C. for up to three months.

Thrombosis Research, 6, 543–548 (1975) describes collection of blook in the presence of EDTA and theophylline but requires centrifugation at 0° C.

Thrombosis Research, 12, 851–861 (1978) describes the collection of blood for PF4 analysis in the presence of platelet release inhibitor EDTA, prostoglandin E, and theophylline. This procedure also requires inconvenient centrifugation at low temperature.

Niemetz, et al, Proc. Soc. Exp. Biol. Med, 128, 658 (1968) describes the effects of various anesthetics on clot retraction, adenosine diphosphate and thrombin-induced platelet aggregation. In those studies it was found that p-aminobenzoyldiethylaminoethanol hydrochloride (Procaine) and related homologs such as p-aminobenzoyldibutylaminoethanol (Butacaine) and p-butylaminobenzoyldimethylaminoethanol (Tetracaine) inhibited thrombin-induced platelet aggregation. Butacaine and tetracaine inhibited ADP-induced platelet aggregation while Procaine did not. Butacaine, tetracaine and procaine inhibited thrombin-induced platelet aggregation. Unexpectedly it has now been found that procaine and not butacaine and tetracaine inhibit the release of platelet factor 4 during the collection process.

BRIEF DESCRIPTION OF THE INVENTION

This invention describes apparatus and methods for inhibiting the platelet release reaction caused by in vitro handling of blood samples and therefore provides a blood sample where plasma components such as platelet factor 4 are a result of in vivo release. It has been discovered that p-aminobenzoyldiethylaminoethanol and the biologically acceptable acid addition salts thereof (Procaine) are unexpectedly effective in inhibiting the platelet release reaction and greatly facilitates handling of blood samples at room temperature for subsequent analysis for platelet release components such as platelet factor 4.

DETAILED DESCRIPTION OF THE INVENTION p-Aminobenzoyldiethylaminoethanol and the biologically acceptable acid addition salts thereof have been found to be particularly effective in inhibiting the platelet release reaction. Generally a final concentration in the blood of about 10–30 millimolar are effective in inhibiting the platelet release reaction with about 15 millimolar being a preferred effective amount. Biologically acceptable acid addition salts refers to a large variety of organic and mineral acid salts such as hydrochloric, hydrobromic, hydroiodic, sulfuric, phosphoric, nitric, acetic, benzoic, toluenesulfonic, formic acids and the like which are useful in preparing addition salts which do not destroy biological activity of proteins such as platelet factor 4.

In a preferred embodiment 2-chloroadenosine in concentrations of about 0.05–1 millimolar, preferably about 0.1 millimolar is used in combination with p-aminobenzoyldiethylaminoethanol hydrochloride to provide a particularly effective stabilizing reagent.

These reagents are conveniently used in a conventional partially evacuated blood collection device containing anticoagulants such as ethylenediaminetetraacetic acid (EDTA). Thus conventional blood collecting devices can be injected with effective amounts of the above-described platelet release inhibiting agents or the device can be manufactured to contain these ingredients initially.

In a broad context the invention encompasses a partially evacuated blood collection device containing an effective amount of p-aminobenzoyldiethylaminoethanol or the biologically acceptable acid addition salts thereof to inhibit the platelet release reaction. In particular the invention encompasses a partially evacuated siliconized stoppered glass tube containing EDTA as an anticoagulant and effective amounts of 2-chloroadenosine and p-aminobenzoyldiethylaminoethanol or the biologically acceptable acid addition salts thereof to inhibit the platelet release reaction.

A most preferred embodiment is a 10 ml partially evacuated stoppered glass tube for blood collecting containing 0.6 ml of a reagent comprising 2.50% EDTA, 0.025% 2-chloroadenosine, 6.60% p-aminobenzoyldiethylaminoethanol hydrochloride, 0.3% sodium chloride having the pH adjusted to 6.5 with sodium hydroxide. The above-listed percents are weight-/volume percents.

Methods and devices of the present invention are particularly useful in platelet factor 4 determinations, in that sample collection and handling are greatly facilitated; for example, centrifugation at low temperature is not required.

Using standard venipuncture techniques for multiple sampling two blood samples are drawn. The first is drawn to clear the system of activating factors, and the second is drawn into the above-identified most preferred embodiment. The sample is mixed by gentle inversion and the tube transferred to an ice bath to incubate for at least thirty minutes (no longer than two hours). The tube is then centrifuged at room temperature at 2500×g for twenty minutes or 1500×g for thirty minutes with a plasma separator. The plasma is transferred to a plastic tube with a plastic pipette. The sample may be stored at 2°–4° C. for 24 hours or at −20° C. for up to three months.

Platelet factor 4 is determined by conventional radioimmunoassay techniques. Using methods and devices of this invention platelet factor 4 normal levels are less than 5 ng/ml. Patients with coronary artery disease, post-heart valve surgery, post-coronary bypass surgery, post-myocardial infarction, and diabetes have elevated levels of platelet factor 4 ranging as high as 100 ng/ml.

We claim:

1. In a method for determining platelet factor 4 in a blood sample the improvement comprising treating the blood sample with an effective amount of p-aminobenzoyldiethylaminoethanol or the biologically acceptable acid addition salts thereof to inhibit the in vitro release of platelet factor 4.

2. A partially evacuated blood collection device containing EDTA as an anticoagulant and an effective amount of 2-chloroadenosine and p-aminobenzoyldiethylaminoethanol or the acid addition salts thereof to inhibit in vitro platelet release of platelet factor 4.

* * * * *